US00PP16055P3

(12) United States Plant Patent
Iwaki

(10) Patent No.: US PP16,055 P3
(45) Date of Patent: Oct. 25, 2005

(54) *TORENIA* PLANT NAMED 'SUNRENILAPA'

(50) Latin Name: ***Torenia* hybrid**
Varietal Denomination: Sunrenilapa

(75) Inventor: Kazunari Iwaki, Omi-hachiman (JP)

(73) Assignee: Suntory Flowers Limited, Tokyo (JP)

( * ) Notice: Subject to any disclaimer, the term of this patent is extended or adjusted under 35 U.S.C. 154(b) by 217 days.

(21) Appl. No.: 10/675,222

(22) Filed: Sep. 29, 2003

(65) Prior Publication Data

US 2005/0071904 P1 Mar. 31, 2005

(51) Int. Cl.[7] ..... A01H 5/00
(52) U.S. Cl. ..... Plt./263
(58) Field of Search ..... Plt./263

(56) References Cited

U.S. PATENT DOCUMENTS

PP10,843 P 3/1999 Tamura et al.
2003/0150033 P1 8/2003 Miyazaki

OTHER PUBLICATIONS

U.S. Appl. No. 10/066,739.

*Primary Examiner*—Kent Bell
(74) *Attorney, Agent, or Firm*—Christie, Parker and Hale, LLP

(57) ABSTRACT

Disclosed herein is a *Torenia* plant that displays large globose flowers having strong purplish-red with moderate purplish-pink petals and a strong reddish-purple floral tube. The plant has a semi-erect growth habit and medium branching. A great profusion of blooms is formed with the entire of plant for a considerable period of time.

2 Drawing Sheets

Botanical/commercial classification: *Torenia* hybrid/*Torenia* Plant.
Varietal denomination: CV. 'Sunrenilapa'.

BACKGROUND OF THE VARIETY

The present invention relates to a new and distinct variety of *Torenia* plant that was obtained from the artificial chromosome doubling of 'Sunreniririepa' (*Torenia* hybrid), obtained by colchicine solution treatment ("artificial doubling").

The *Torenia* is a very popular plant and is used for flower bedding and potting in the summer season. There are only a few varieties of the *Torenia* plant that have a semi-erect growth habit, medium branching, and a great profusion of blooms.

Accordingly, this invention was aimed at obtaining a new variety having large globose form flowers, strong purplish-red with moderate purplish-pink petals, a semi-erect growth habit, medium branching and a great profusion of blooms.

The new variety of the *Torenia* plant of this invention originated from the artificial doubling of 'Sunreniririepa' that was previously filed in Japan and the United States of America.

In September 1998, the cuttings of 'Sunreniririepa' were treated with 0.1% colchicines solution, which were propagated by the use of cuttings on the peat at Yokaichi, Shiga, Japan. After two months, some survived plantlets were transplanted in pots. In December 1998, colchiploids were obtained from the cultivation. The discovered *Torenia* plants were propagated by the use of cuttings and then grown in beds and pots on trial. The botanical characteristics of the plants were examined using the parent variety 'Sunreniririepa' (U.S. Plant Pat. No. 14,302) and the similar variety 'Sunrenilabu' (U.S. Plant Pat. No. 10,843) for comparison. As a result, one plant was selected in view of flower size and color, and its growth habit, and it was concluded that the finally selected plant is distinguishable from any other variety whose existence is known to us and is uniform and stable in its characteristics. The new variety reproduces true to type in successive generations of asexual reproduction. The new variety has been named 'Sunrenilapa'.

In the following description the color-coding is in accordance with The R.H.S. Colour Chart of The Royal Horticultural Society, London, England.

The main botanical characteristics of the parent variety 'Sunreniririepa' are as follows;

Plant:
- *Growth habit*.—Semi-erect. The stems hang down pliantly when potted in a hanging pot.
- *Plant height*.—Approximately 20 cm.
- *Plant extension*.—Approximately 55 cm.
- *Growth*.—Medium branching, a great profusion of blooms; the entire bush remaining in bloom for a considerable period of time.
- *Blooming period*.—June to November in the southern Kanto area, Japan. The plant shape does not change throughout this period.

Stem:
- *Diameter*.—Approximately 2.5 mm.
- *Anthocyanin pigmentation*.—Present.
- *Branching*.—Medium.
- *Pubescence*.—Sparse.
- *Length of internode*.—Approximately 3.1 cm.

Leaf:
- *Phyllotaxis*.—Opposite.
- *Shape of blade*.—Lanceolate.
- *Length*.—Approximately 2.9 cm.
- *Width*.—Approximately 1.9 cm.
- *Depth of incision*.—Medium.
- *Color*. (*upper side*).—R.H.S. 137A (Moderate olive-green).
- *Pubescence of upper side*.—Sparse.

Flower:
*Facing direction*.—Lateral.
*Diameter*.—Approximately 26 mm.
*Height*.—Approximately 28 mm.
*Color of floral tube*.—R.H.S. 78A (Strong reddish-purple).
*Color of petal*.—Single color; R.H.S. 78A (Strong reddish-purple).
*Yellow eye color*.—Absent.
*Calyx*.—Approximately 1.5 cm in length.
*Anthocyanin pigmentation of calyx limb*.—Present.
*Peduncle*.—Approximately 1.7 mm in thickness; and Approximately 2.2 cm in length.
*Reproductive organs*.—1 pistil and 4 stamens.
*Anther color*.—White.
*Flowering duration*.—Medium.
Physiological and ecological characteristics: Medium resistance to diseases and pests, high moderate tolerance to heat and low tolerance to cold. The plant grows and has flowers commonly when grown in the shade of trees.

The botanical characteristics of the comparison variety 'Sunrenilabu' is as follows:

Plant:
*Growth habit*.—Semi-erect. The stems hang down pliantly when potted in a hanging pot.
*Plant height*.—Approximately 15.0 cm.
*Plant extension*.—Approximately 70 cm.
*Growth*.—Medium branching, a great profusion of blooms; the entire bush remaining in bloom for a considerable period of time.
*Blooming period*.—June to November in the southern Kanto area, Japan. The plant shape does not change throughout this period.
Stem:
*Diameter*.—Approximately 2.0 mm.
*Anthocyanin pigmentation*.—Present.
*Branching*.—Medium.
*Pubescence*.—Sparse.
*Length of internode*.—Approximately 6.0 cm.
Leaf:
*Phyllotaxis*.—Opposite.
*Shape of blade*.—Serrate.
*Length*.—Approximately 3.0 cm.
*Width*.—Approximately 2.5 cm.
*Depth of incision*.—Medium.
*Color*. (*upper side*).—R.H.S. 137A (Moderate olive-green).
*Pubescence of upper side*.—Sparse.
Flower:
*Facing direction*.—Lateral.
*Diameter*.—Approximately 35 mm.
*Height*.—Approximately 25 mm.
*Color of floral tube*.—R.H.S. 85A (Light purple).
*Color of petal*.—Bi-color; upper petal: R.H.S. 85A (Light purple); Lower petal: R.H.S. 84A (Deep purple); Right and left petals: R.H.S. 87A (Vivid purple).
*Yellow eye color*.—Absent.
*Calyx*.—Approximately 2.2 cm in length.
*Anthocyanin pigmentation of calyx limb*.—Present.
*Peduncle*.—Approximately 2.5 mm in thickness; and Approximately 2.5 cm in length.
*Reproductive organs*.—1 pistil and 4 stamens.
*Anther color*.—White.
*Flowering duration*.—Medium.
Physiological and ecological characteristics: Medium resistance to diseases and pests, high tolerance to heat and low tolerance to cold. The plant grows and has flowers commonly when grown in the shade of trees.

SUMMARY OF THE VARIETY

The new 'Sunrenilapa' plant has a semi-erect habit, large globose form flowers having strong purplish-red with moderate purplish-pink petals. The new plant displays medium branching and forms a great profusion of blooms, and the entire bush remains in bloom for a considerable period of time.

The new variety of the present invention has been asexually reproduced by the use of cuttings at Shiga, Japan. Such propagation has confirmed that the characteristics are firmly fixed and are reliably transmitted to subsequent generation. The new variety reproduces true to type in successive generations of asexual reproduction.

DESCRIPTION OF THE VARIETY

Figure 1:
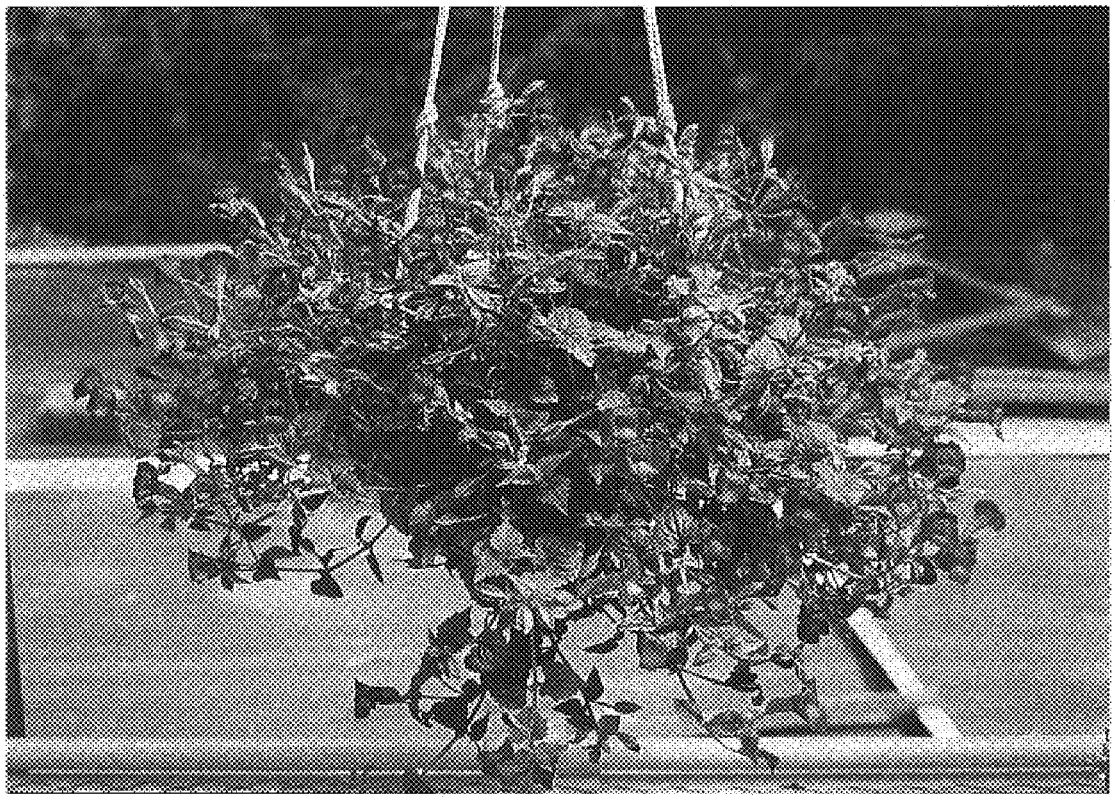
FIG. 1 is a photograph showing a partial view of the new variety of *Torenia* plant 'Sunrenilapa' planted in a flower pot.
Figure 2:
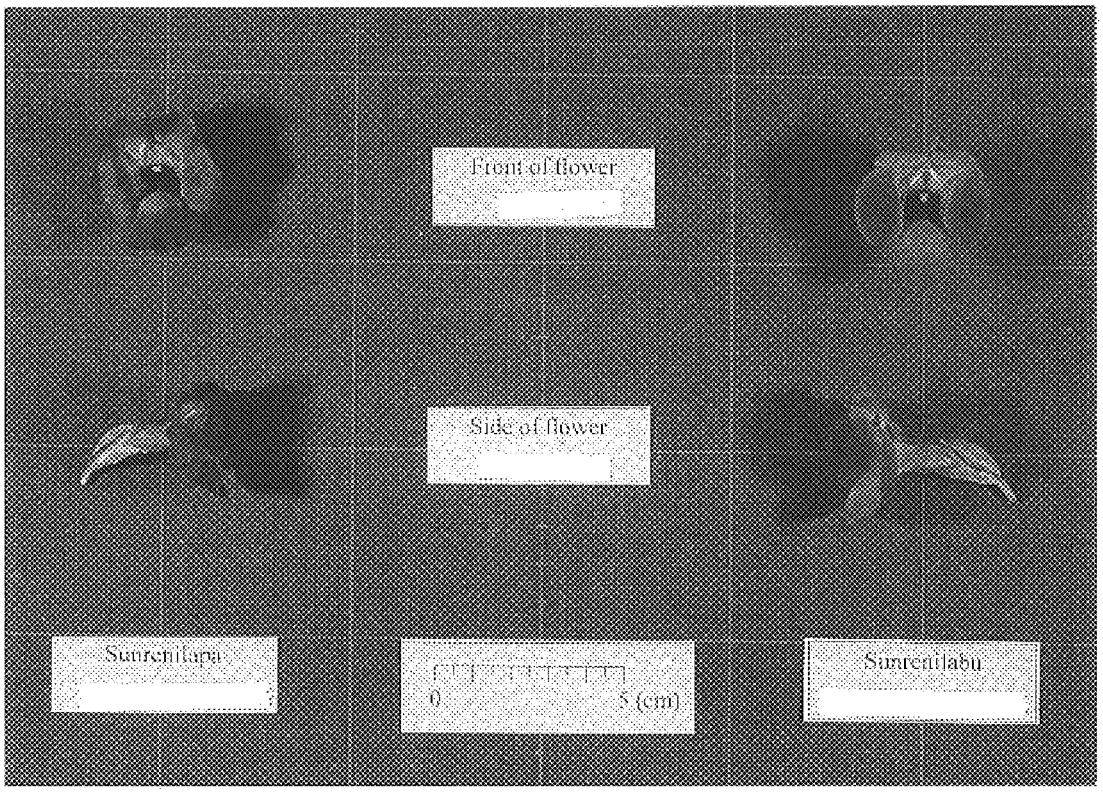
FIG. 2 is a photograph of flowers of the new variety of *Torenia* plant 'Sunrenilapa' and those of the comparable variety 'Sunrenilabu'.

The botanical characteristics of the new and distinct variety of the *Torenia* plant 'Sunrenilapa' are set forth hereafter. The plant was observed at the end of August while growing at Yokaichi-shi, Shiga, Japan. Young plants were placed in a flower bedding at a spacing of 6 plants per square meter, and in pots with 3 plants being placed in each 30 cm pot. All plants described herein were observed after approximately three months of growth.

Plant:
*Growth habit*.—Semi-erect. The stems hang down pliantly when potted in a hanging pot.
*Plant height*.—Approximately 25 cm.
*Spreading area of the plant*.—Approximately 40 cm.
*Growth*.—Medium branching, a great profusion of blooms; the entire bush remaining in bloom for a considerable period of time.
*Blooming period*.—June to November in the southern Kanto area, Japan. The plant shape does not change throughout this period.
Stem:
*Length*.—Approximately 20 cm.
*Diameter*.—Approximately 2.2 mm.
*Color*.—Near R.H.S. 144B.
*Branching*.—Medium.
*Pubescence*.—Sparse.
*Length of internode*.—Approximately 5.5 cm.
Leaf:
*Phyllotaxis*.—Opposite.
*Shape of blade*.—Lanceolate.
*Apex*.—Obtuse.
*Base*.—Truncate.
*Length*.—Approximately 3.5 cm.
*Width*.—Approximately 2.5 cm.
*Margin*.—Crenate.

*Depth of incision*.—Medium.
*Color*. (*upper side*).—R.H.S. 147A (Grayish olive green). (Under side) — Near R.H.S. 138B.
*Pubescence of upper side*.—Sparse.
*Thickness of petiole*.—Approximately 1.3 mm.
*Length of petiole*.—Approximately 0.7 cm.
*Petiole color*.—Near R.H.S. 144C.

Flower:
*Bud*.—Shape — Ellipsoidal.
*Length*.—Approximately 1.6 cm.
*Diameter*.—Approximately 0.8 cm.
*Color*.—Near R.H.S. 143A.
*Floral tube diameter*.—Approximately 1.0 cm.
*Inflorescence peduncles*.—Axillary.
*Flower form*.—Globose.
*Flower depth* (*height*).—Approximately 3.7 cm.
*Flower length*.—Approximately 35 mm.
*Flower width*.—Approximately 30 mm.
*Length of tube*.—Approximately 45 mm.
*Color of floral tube*.—(Outer surface) near R.H.S. 72A (Strong reddish-purple.); (Inner surface) near R.H.S. N78A; vertical lines on the inner surface of floral tube — Near R.N.S. 79B.

Petal:
*Number*.—4.
*Shape*.—Elliptic.
*Length*.—Upper — approximately 1.0 cm; Side — approximately 1.6 cm; Lower — approximately 1.0 cm.
*Width*.—Upper — approximately 2.1 cm; side — approximately 0.7 cm; lower — approximately 1.9 cm.
*Apex shape*.—Round.
*Base shape*.—Fused.
*Margin*.—Entire. Upper petal is undulated.
*Texture*.—Smooth.
*Color of petal*.—Upper surface — near R.H.S. 70A (Strong purplish-red.), lower surface — near R.H.S. N78A; margin — near R.H.S. N79B; R.H.S. 65A (Moderate purplish-red) at base of petal near throat.
*Upper bilabiate petal wave*.—Strong.

Calyx:
*Calyx shape*.—Deeply 2-lobed.
*Calyx diameter*.—Approximately 7.0 mm.
*Color*.—Outer surface — Near R.H.S. 143A; Inner surface — near R.H.S. 143A.
*Degree of development of wings*.—Medium.
*Calyx length*.—Approximately 17 mm.
*Anthocyanin pigmentation of calyx limb*.—Absent.
*Anther color*.—Near R.H.S. N78C.
*Anther spur*.—Present.
*Anther color*.—White.
*Peduncle thickness*.—Approximately 2.0 mm.
*Peduncle color*.—Near R.H.S. 144B.
*Peduncle length*.—Approximately 1.5 mm.
*Inflorescence type*.—Flower solitary, axillary and terminal.
*Number of flowers per stem*.—Approximately 3.
*Reproductive organs*.—1 pistil and 4 stamens.
*Flowering duration*.—June to November in the southern Kanto area, Japan.
*Lastingness of bloom*.—Approximately three days.

Resistance: Displays moderate resistance to powdery mildew and significant resistance to spider mite when compared to other *Torenia* varieties.

*Hardiness*.—Susceptible to damage under 5° C. The plant grows well at temperatures up to 30° C. The lowest temperature for the plant survival has not been evaluated.

The plant grows and has flowers commonly when grown in the shade of trees.

*Seeds*.—Not observed.
*Pedicel*.—None.

This new 'Sunrenilapa' variety is particularly suitable for growing in flower beds and pots, as well as hanging baskets.

I claim:

1. A new and distinct *Torenia* plant named 'Sunrenilapa', substantially as herein illustrated and described.

* * * * *